(12) United States Patent  
Zhu et al.

(10) Patent No.: US 11,119,085 B2  
(45) Date of Patent: Sep. 14, 2021

(54) METHODS AND DEVICES FOR DETECTING MERCURY ISOTOPES IN OIL-GAS SOURCES

(71) Applicant: PETROCHINA COMPANY LIMITED, Beijing (CN)

(72) Inventors: Guangyou Zhu, Beijing (CN); Shunlin Tang, Beijing (CN)

(73) Assignee: PetroChina Company Limited, Beijing (CN)

( * ) Notice: Subject to any disclaimer, the term of this patent is extended or adjusted under 35 U.S.C. 154(b) by 293 days.

(21) Appl. No.: 16/392,812

(22) Filed: Apr. 24, 2019

(65) Prior Publication Data

US 2020/0132649 A1  Apr. 30, 2020

(30) Foreign Application Priority Data

Oct. 31, 2018 (CN) .......................... 201811283982.4

(51) Int. Cl.
*G01N 33/28* (2006.01)  
*G01N 33/22* (2006.01)  
(Continued)

(52) U.S. Cl.
CPC ..... *G01N 33/0045* (2013.01); *G01N 21/6404* (2013.01); *G01N 33/225* (2013.01); *G01N 33/2835* (2013.01)

(58) Field of Classification Search
CPC .......... G01N 21/6404; G01N 33/0045; G01N 33/22; G01N 33/225; G01N 33/2835;
(Continued)

(56) References Cited

U.S. PATENT DOCUMENTS 3,865,549 A  2/1975 Riley  
4,758,519 A  7/1988 Nakao et al.  
(Continued)

FOREIGN PATENT DOCUMENTS

AU  2019202479 B1  4/2020  
CN  2684180 Y  3/2005  
(Continued)

OTHER PUBLICATIONS

Zheng et al. Journal of Analytical Atomic Spectrometry, vol. 22, Jul. 30, 2007, pp. 1097-1104.*

(Continued)

*Primary Examiner* — Maureen Wallenhorst  
(74) *Attorney, Agent, or Firm* — Foley & Lardner LLP

(57) ABSTRACT

A method and device for detecting mercury isotopes in an oil-gas source. The device includes at least one enrichment-absorption system for mercury in crude oil/hydrocarbon source rock, an enrichment-absorption system for mercury in natural gas and at least one secondary purification-enrichment system for mercury. The enrichment-absorption system for mercury in crude oil/hydrocarbon source rock includes three air-absorption bottles, a pyrolysis/cracking system, five impact samplers, and a vacuum pump, which are connected in series by pipe lines. The enrichment-absorption system for mercury in natural gas includes five impact samplers connected in series, wherein the first impact sampler is connected to the natural gas outlet from the natural gas well and the last impact sampler is connected to the cumulative gas flow meter.

19 Claims, 2 Drawing Sheets

(51) Int. Cl.
  *G01N 33/00* (2006.01)
  *G01N 21/64* (2006.01)
(58) Field of Classification Search
  CPC ..... G01N 33/20; Y10T 436/24; Y10T 436/25; Y10T 436/25375; Y10T 436/255
  USPC .. 436/60, 73, 77, 79, 81, 84, 164, 172, 173, 436/174, 177, 178, 181; 422/82.05, 422/82.08, 527, 88
  See application file for complete search history.

(56) References Cited

U.S. PATENT DOCUMENTS

| | | | |
|---|---|---|---|
| 5,733,786 A * | 3/1998 | Green | G01N 31/22 422/504 |
| 6,197,269 B1 | 3/2001 | Jansen et al. | |
| 7,144,736 B2 * | 12/2006 | Noda | G01N 1/2247 436/81 |
| 8,992,769 B2 * | 3/2015 | O'Rear | C10G 29/02 208/251 R |
| 9,125,596 B2 | 9/2015 | Leclerc et al. | |
| 9,574,140 B2 * | 2/2017 | Lord, III | G01N 33/2858 |
| 9,712,035 B1 | 7/2017 | Bango et al. | |
| 9,988,584 B2 | 6/2018 | Oehr | |
| 10,816,532 B2 * | 10/2020 | Zhu | G01N 21/3103 |
| 2002/0033097 A1 | 3/2002 | El-Shoubary et al. | |
| 2004/0237634 A1 * | 12/2004 | Makino | B01D 53/8665 73/61.52 |
| 2006/0021506 A1 | 2/2006 | Hakka et al. | |
| 2009/0004644 A1 | 1/2009 | Kiel et al. | |
| 2009/0169450 A1 | 7/2009 | Naito et al. | |
| 2010/0126909 A1 | 5/2010 | Bhasin et al. | |
| 2012/0067786 A1 | 3/2012 | Gallup et al. | |
| 2012/0205533 A1 | 8/2012 | Ariya et al. | |
| 2013/0281553 A1 | 10/2013 | Kubic et al. | |
| 2013/0306311 A1 | 11/2013 | Cooper et al. | |
| 2014/0262955 A1 | 9/2014 | Cooper et al. | |
| 2015/0047465 A1 | 2/2015 | Langley | |
| 2015/0050344 A1 | 2/2015 | Watson et al. | |
| 2015/0108040 A1 | 4/2015 | Lord et al. | |
| 2015/0218462 A1 | 8/2015 | Lord et al. | |
| 2016/0003023 A1 | 1/2016 | O'Rear et al. | |
| 2016/0045841 A1 | 2/2016 | Kaplan et al. | |
| 2016/0122658 A1 | 5/2016 | O'Rear et al. | |
| 2018/0340174 A1 | 11/2018 | Lundorf et al. | |
| 2019/0275464 A1 | 9/2019 | Mazyck et al. | |
| 2020/0132649 A1 | 4/2020 | Zhu et al. | |

FOREIGN PATENT DOCUMENTS

| | | |
|---|---|---|
| CN | 201529482 U | 7/2010 |
| CN | 201740738 U | 2/2011 |
| CN | 102608271 A | 7/2012 |
| CN | 202533285 U | 11/2012 |
| CN | 103149057 A | 6/2013 |
| CN | 103293326 A | 9/2013 |
| CN | 103592159 | 2/2014 |
| CN | 104181014 | 12/2014 |
| CN | 104297173 A | 1/2015 |
| CN | 104297174 A | 1/2015 |
| CN | 204346807 U | 5/2015 |
| CN | 105699160 A | 6/2016 |
| CN | 107389387 A | 11/2017 |
| CN | 107817236 | 3/2018 |
| CN | 108020601 A | 5/2018 |
| CN | 207540976 U | 6/2018 |
| CN | 207585997 U | 7/2018 |
| CN | 108956238 * | 12/2018 |
| CN | 109142017 * | 1/2019 |
| EP | 1 324 034 A1 | 7/2003 |
| FR | 2044482 A5 | 2/1971 |
| JP | 2003-240687 A | 8/2003 |
| JP | 2016-070726 A | 5/2016 |
| KR | 2010-0047725 A | 5/2010 |
| WO | WO-2016/108766 A1 | 7/2016 |

OTHER PUBLICATIONS

Brombach et al. Talanta, vol. 199, Feb. 20, 2019, pp. 277-284.*
English-language Abstract of Chen, Gengliang, "Standardization of Mercury Determination in Natural Gas," Petroleum Planning & Engineering, vol. 8, No. 1, 4 pages (Jan. 1997).
English-language Abstract of Deng et al., "Analysis on Mercury Forms in Oil and Gas," Oil and Gas Treating and Processing, vol. 31, No. 5, 5 pages (Oct. 2013).
English-language Abstract of Duan et al., "Experimental Study on Mercury Release and Adsorption During Coal Pyrolysis," PTCA Journal of Taiyuan University of Technology, vol. 41, No. 5, 3 pages (Sep. 2010).
English-language Abstract of Leng et al., "Discussion on Analysis Method of Trace Mercury in Liquefied Natural Gas," Guangzhou Chemical Industry, vol. 42, No. 23, 3 pages (Dec. 2014).
English-language Abstract of Li, "Determination of Mercury in Crude Oil by Cold Atomic Absorption Spectrometry," Chinese Journal of Spectroscopy Laboratory, vol. 21, No. 4, 3 pages (Jul. 2004).
English-language Abstract of Liu et al., "Advance of Research on Mercury and its Compounds Collecting and Measuring Methods," Natural Gas Geoscience, vol. 17, No. 4, 7 pages (Aug. 2006).
English-language Abstract of Tu, "Preliminary Study on Mercury Occurrence in Source Rocks," ACTA Sedimentolgica Sinica, vol. 3, No. 1, 7 pages (Jan. 1985).
English-language Abstract of Wang et al., "AFS Determination of Pb, As, and Hg in Crude Oil with Microwave Assisted Sample Digestion," PTCA (Part B: Chem. Anal.), vol. 48, No. 9, 3 pages (2012).
English-language Abstract of Wei et al., "An Introduction to XG-7Z Zeeman Mercury Measurement Instrument and the Analytical Method for Trace Concentrations of Mercury," Geophysical &Geochemical Exploration, vol. 38, No. 2, 8 pages (Apr. 2014).
English-language Abstract of Xue, "Research Progress on Analytical Methods of Mercury in Petroleum," Petroleum and Petrochemical Today, vol. 16, No. 6, 4 pages (Jun. 2008).
English-language translation of National Environmental Protection Standard of the People's Republic (HJ 543-2009): Stationary source emission-determiniation of mercury—cold atomic absorption spectrophotometry, 4 pages (Dec. 30, 2009).
English-language translation of National Standard of the People's Republic (GB/T 16157-1996): The determination of particulates and sampling methods of gaseous pollutants emitted from exhaust gas of stationary source, 4 pages (Mar. 6, 1996).
English-language translation of Paragraph 5, p. 10 of Xinliang, Zhao, "Experimental Study on the Transformation of Mercury Element During Coal Pyrolysis Gasification," Huazhong University of Science and Technology Master's Thesis, 3 pages (Jan. 2012).
Australian First Examination Report, App. No. 2019202479, PetroChina Company Limited, 6 pages (dated Nov. 20, 2019).
Australian First Examination Report, App. No. 2019202485, PetroChina Company Limited, 6 pages (dated Nov. 29, 2019).
Brahma, N., "The on line determination of mercury in process streams using atomic spectrometry," Ph.D. Thesis, University of Plymouth (Plymouth, United Kingdom), 249 pages (Nov. 2000).
Hoffart et al., "A two-step acid mercury removal process for pulverized coal," Fuel, vol. 85. pp. 1166-1173 (2006).
Lopez-Anton et al., "Analytical methods for mercury analysis in coal and coal combustion by-products," Int'l Journal of Coal Geology, 94, 47 pages (2012).
Smith, C., "Isotopic geochemistry of mercury in active and fossil hydrothermal systems," Ph.D. Thesis, University of Michigan (Ann Arbor, Michigan), 174 pages (2010).
Australian First Examination Report, App. No. 2019202470, PetroChina Company Limited, 5 pages (dated Apr. 16, 2020).
First Office Action for CN App. No. 201811283982.4 dated Sep. 3, 2020 (26 pages).
Li et al., "Volatility and Speculation of Mercury during Pyrolysis and Gasification of Five Chinese coals", Energy Fuels, vol. 25, No. 9, Jul. 11, 2012, pp. 3988-3996 (9 pages).

(56) References Cited

OTHER PUBLICATIONS

Roy et al., "Nitrogen Oxides, Sulfur Trioxide, and Mercury Emissions during Oxy-fuel Fluidized Bed Combustion of Victorian Brown Coal", Environmental Science & Technology, vol. 48, 2014, p. 14844-14850 (7 pages).
Search Report for CN App. No. 201811283982.4 dated Aug. 28, 2020 (8 pages).
Sheng et al., "Prevention of mercury damage", Petrochemical Industry Press, Jan. 1978, pp. 78-79 (6 pages).
Office Action for CA App. No. 3039714 dated Apr. 23, 2021 (3 pages).
Office Action for CA App. No. 3039714 dated Aug. 13, 2020 (5 pages).

* cited by examiner

METHODS AND DEVICES FOR DETECTING MERCURY ISOTOPES IN OIL-GAS SOURCES

CROSS-REFERENCE TO RELATED PATENT APPLICATIONS

This application claims the benefit of Chinese Patent Application No. 201811283982.4, filed Oct. 31, 2018, which is incorporated herein by reference in its entirety.

TECHNICAL FIELD

The invention relates to a technical field of oil-gas exploration. In particular, to the present invention relates to a method and a device for detecting mercury isotopes in an oil-gas source.

BACKGROUND

Studies of organic geochemistry, the composition, structure, origin and evolution of an organic matter in geological bodies are mainly concerned. In the field of oil and gas exploration, particularly, the oil-gas genesis and oil source correlation are very important, which is related to evaluation of exploration targets, optimization of well location and scale and distribution of oil-gas reservoirs and so on, and thus is highly appreciated. The common methods are to determine the oil-gas genesis and source by index such as biomarker and carbon isotope, which are successful in most area or oil-gas fields. However, as for some complicated areas, such as the Tarim Basin, there always exists dispute whether the oil and gas are from Cambrian or Ordovician. Therefore, it is necessary to develop a new index system to determine the oil-gas genesis.

Mercury is easily adsorbed and sequestered by organic matter, and is considered to have a binding level with the organic matter as close as that between mercury and sulfur. Thus, mercury is easily enriched in the source rock, which enters oil and gas in the hydrocarbon forming process and migrates with the oil and gas. Therefore, mercury is associated with processes such as formation of deposited organic matter, thermal-maturity hydrocarbon generation, migration and accumulation, and is important in tracer value. There are certain differences in the stable-mercury-isotope information in source rocks and oil-gas from different basin areas, different genetic types and different thermal evolution stages, which can be used to identify the oil-gas genesis and guide oil-gas exploration.

SUMMARY

An object of the present disclosure is to provide a device for detecting mercury isotopes in an oil-gas source.

Another object of the present disclosure is to provide a method for detecting mercury isotopes in an oil-gas source.

In order to achieve the above object, in one aspect, the present disclosure provides a device for detecting mercury isotopes in an oil-gas source, comprising: at least one enrichment-absorption system 1 for mercury in crude oil/hydrocarbon source rock, an enrichment-absorption system 2 for mercury in natural gas and at least one secondary purification-enrichment system 3 for mercury; the enrichment-absorption system 1 for mercury in crude oil/hydrocarbon source rock comprises three air-absorption bottles, a pyrolysis/cracking system 12, five impact samplers, and a vacuum pump 14, which are connected in series by pipe lines; the enrichment-absorption system 2 for mercury in natural gas comprises five impact samplers connected in series, wherein the first impact sampler is connected to the natural gas outlet from the natural gas well and the last impact sampler is connected to the cumulative gas flow meter 26; the secondary purification-enrichment system 3 for mercury comprises a nitrogen-gas cylinder 31, a collection bottle 32 with potassium permanganate absorption liquid in which mercury isotope is absorbed, and a secondary enrichment-absorption bottle 33 containing an acidic aqueous potassium permanganate solution, which are connected in series by pipe lines, wherein the secondary purification-enrichment system 3 further comprises a stannous-chloride storage bottle 34, which is connected with a pipe line between the nitrogen-gas cylinder and the collection bottle 32 with potassium-permanganate absorption liquid via a peristaltic pump 35 and through a pipe line.

In accordance with some specific embodiments, in the device, the five impact samplers in the enrichment-absorption system 1 for mercury in crude oil/hydrocarbon source rock are, in the connection order, respectively a first impact sampler 131 containing a stannous chloride solution, an empty impact sampler 132, a third impact sampler 133 containing an acidic potassium permanganate solution, a fourth impact sampler 134 containing an aqueous sodium hydroxide solution and an fifth impact sampler 135 containing a silica gel, wherein the first impact sampler 131 is connected via a pipe line to the pyrolysis/cracking system 12.

The five impact samplers in the enrichment-absorption system 2 for mercury in natural gas are, in the connection order, respectively an empty sixth impact sampler 21 and a seventh impact sampler 22 containing an acidic aqueous potassium permanganate solution, an eighth impact sampler 23 containing an acidic aqueous potassium permanganate solution, a ninth impact sampler 24 containing an acidic aqueous potassium permanganate solution, and a tenth impact sampler 25 containing a silica gel.

In accordance with some specific embodiments, in the device, the three air-absorption bottles in the enrichment-absorption system 1 for mercury in crude oil/hydrocarbon source rock are, in the connection order, respectively a first air-absorption bottle 111 containing aqua regia, a second air-absorption bottle 112 containing aqua regia and a third air-absorption bottle 113 containing an aqueous sodium hydroxide solution, and the pyrolysis/cracking system 12 is connected to the third air-absorption bottle 113 through a pipe line.

In accordance with some specific embodiments, in the device, the pyrolysis/cracking system 12 comprises a pyrolysis chamber 121 and a cracking chamber 122 connected in series with pipe lines; said pyrolysis chamber 121 is connected via a pipe line to the last air-absorption bottle in the connection order in the enrichment-absorption system 1 for mercury in crude oil/hydrocarbon source rock, and the cracking chamber 122 is connected via a pipe line to the first impact sampler in the connection order in the enrichment-absorption system 1 for mercury in crude oil/hydrocarbon source rock.

In accordance with some specific embodiments according to the present invention, in the device, each of the three air-absorption bottles and five impact samplers in the enrichment-absorption system 1 for mercury in crude oil/hydrocarbon source rock, and the five impact samplers in the enrichment-absorption system 2 for mercury in natural gas is a borosilicate glass bottle and is provided with a gas inlet and a gas outlet at the respective top thereof, wherein the gas inlet communicates with the inner space of the bottle through a glass tube which is provided inside the bottle and extends to the lower part of the bottle.

In accordance with some specific embodiments, in the device, in the enrichment-absorption system 1 for mercury in crude oil/hydrocarbon source rock, three air-absorption bottles are connected in series, with the gas outlet of the former air-absorption bottle connected to the gas inlet of the latter air-absorption bottle via a pipe line, the gas inlet of the first air-absorption bottle communicating with air, and the gas outlet of the last air-absorption bottle connected to the pyrolysis/cracking system 12 by a pipe line; the five impact samplers are connected in series, with the gas outlet of the former impact sampler connected to the gas inlet of the latter impact sampler by a pipe line, the gas inlet of the first impact sampler connected via a pipe line to the pyrolysis/cracking system 12, and the gas outlet of the last impact sampler connected to the vacuum pump 14 by a pipe line.

In the enrichment-absorption system 2 for mercury in natural gas, the five impact samplers are connected in series, with the gas outlet of the former impact sampler connected to the gas inlet of the latter impact sampler by a pipe line, the gas inlet of the first impact sampler connected to the natural gas outlet from the natural gas well by a pipe line, and the gas outlet of the last impact sampler connected to the cumulative gas flow meter 26 by a pipe line.

In accordance with some specific embodiments, in the device, the secondary purification-enrichment system further comprises a mercury-trapping gold tube 36 which is disposed on a pipe line connecting the nitrogen-gas cylinder 31 and the collection bottle 32 with potassium permanganate absorption liquid, and approximates to the gas outlet of the nitrogen-gas cylinder 31.

In accordance with some specific embodiments, in the device, the acidic aqueous potassium permanganate solution in the enrichment-absorption system 1 for mercury in crude oil/hydrocarbon source rock and the enrichment-absorption system 2 for mercury in natural gas have a potassium permanganate concentration of 1 w/v %, and an acid concentration of 10 v/v %, the acid is sulfuric acid; and the acidic aqueous potassium permanganate solutions in the secondary purification-enrichment system 3 for mercury have a potassium permanganate concentration of potassium permanganate of 4 w/v %, and an acid concentration of 10 v/v %, the acid is sulfuric acid.

In accordance with some specific embodiments, in the device, each of the stannous chloride solution in the enrichment-absorption system 1 for mercury in crude oil/hydrocarbon source rock and the secondary purification-enrichment system 3 independently has a concentration of 15 to 25 w/v %; and the aqueous sodium hydroxide solution in the fourth impact sampler 134 has a concentration of 30 w/v %.

In accordance with some specific embodiments, in the device, the aqueous sodium hydroxide solution in the third air-absorption bottle 113 has a concentration of 30 w/v %.

In accordance with some specific embodiments, the device further comprises a detector for detecting the total mercury content of the mercury enriched in the secondary enrichment-absorption bottle 22 and a detector for detecting the composition of stable isotopes of the mercury enriched in the secondary enrichment-absorption bottle 22.

In accordance with some specific embodiments, in the device, the detector for detecting the total mercury content of the mercury enriched in the secondary enrichment-absorption bottle 22 is a cold atomic fluorescence mercury detector, and the detector for detecting the composition of stable isotopes of the mercury enriched in the secondary enrichment-absorption bottle 22 is a multi-collector inductively-coupled plasma mass spectrometer.

In accordance with some specific embodiments, the device comprises two enrichment-absorption systems 1 for mercury in crude oil/hydrocarbon source rock, and three secondary purification-enrichment systems 3 for mercury, wherein the two enrichment-absorption systems 1 for mercury in crude oil/hydrocarbon source rock are respectively used for the enrichment and absorption for mercury in the crude oil and the enrichment and absorption for mercury in the hydrocarbon source rock; the three secondary purification-enrichment systems 3 for mercury are respectively used for the secondary purification and enrichment for mercury in crude oil, the secondary purification and enrichment for mercury in hydrocarbon source rock, and the secondary purification and enrichment for mercury in natural gas.

In the present disclosure, the two enrichment-absorption system 1 for mercury in crude oil/hydrocarbon source rock, used for the enrichment and absorption for mercury in crude oil and for the enrichment and absorption for mercury in hydrocarbon source rock, may be referred to as an enrichment-absorption system for mercury in crude oil and an enrichment-absorption system for mercury in hydrocarbon source rock, respectively. The secondary purification-enrichment systems for the secondary purification and enrichment for mercury in crude oil, for the secondary purification and enrichment for mercury in hydrocarbon source rock, and for the secondary purification and enrichment for mercury in natural gas may be referred to as a secondary purification-enrichment system for mercury in crude oil, a secondary purification-enrichment system for mercury in hydrocarbon source rock and a secondary purification-enrichment system for mercury in natural gas, respectively.

In accordance with some specific embodiments, in the device, the enrichment-absorption system 1 for mercury in crude oil/hydrocarbon source rock further comprises a sink 114 for air-absorption bottles, in which the three air-absorption bottles in the enrichment-absorption system 1 for mercury in crude oil/hydrocarbon source rock are disposed, and a sink 115 for impact samplers, in which the five impact samplers are disposed.

In accordance with some specific embodiments, in the device, the enrichment-absorption system 2 for mercury in natural gas further comprises a sink 27 for the enrichment-absorption system 2 for mercury in natural gas, in which the five impact samplers in the enrichment-absorption system 2 for mercury in natural gas are disposed.

In accordance with some specific embodiments, in the device, the secondary purification-enrichment system 3 for mercury further comprises a sink 37 for the secondary purification-enrichment system 3 for mercury, in which the collection bottle 32 with potassium permanganate absorption liquid and the secondary enrichment-absorption 33 in the secondary purification-enrichment system 3 for mercury are disposed.

In another aspect, the present disclosure also provides a method for detecting mercury isotopes in an oil-gas source, comprising the steps of:

(1-a) primary enrichment for mercury isotopes in crude oil: heating a crude oil sample to perform pyrolysis and cracking until the crude oil sample is completely cracked, absorbing the gas released by heating the crude oil sample with an acidic aqueous potassium permanganate solution to enrich the mercury element in the crude oil sample, and collecting all of the acidic potassium permanganate solutions in which the mercury element is enriched in step (1-a);

(1-b) purification and enrichment for mercury isotopes in crude oil: reducing the mercury absorbed in the step (1-a) to mercury vapor with a stannous chloride solution, and then purifying and enriching the mercury vapor by using an acidic aqueous potassium permanganate solution;

(1-c) detection for mercury isotopes in crude oil: detecting the acidic potassium permanganate solution in which the mercury vapor is enriched in step (1-b) to determine the total mercury content and the composition/content of stable mercury isotopes therein;

(2-a) primary enrichment for mercury isotopes in hydrocarbon source rock: pulverizing a hydrocarbon source rock sample to 200 mesh, heating to 600° C., subjecting to pyrolysis and cracking until the petroleum in the hydrocarbon source rock sample is completely cracked, absorbing the gas released by heating the petroleum with an acidic aqueous potassium permanganate solution to enrich the mercury element from petroleum in the hydrocarbon source rock sample, and collecting all of the acidic potassium permanganate solutions in which the mercury element is enriched in step (2-a);

(2-b) purification and enrichment for mercury isotopes in hydrocarbon source rock: reducing the mercury absorbed in the step (2-a) to mercury vapor with a stannous chloride solution, and then purifying and enriching the mercury vapor by using an acidic aqueous potassium permanganate solution;

(2-c) collecting mercury isotopes in the hydrocarbon source rock by acid digestion;

(2-d) detection for mercury isotopes in crude oil: detecting the acidic potassium permanganate solutions in which the mercury vapor is enriched in steps (2-b) and (2-c) to determine the total mercury content and the composition/content of stable mercury isotopes therein;

(3-a) primary enrichment for mercury isotopes in natural gas: subjecting natural gas to a three-stage cascading absorption with acidic aqueous potassium permanganate solutions, and collecting all of the acidic aqueous potassium permanganate solutions in which natural gas is absorbed in step (3-a);

(3-b) mercury purification and enrichment: reducing the mercury absorbed in the step (3-a) to mercury vapor with a stannous chloride solution, and then purifying and enriching the mercury vapor by using an acidic potassium permanganate aqueous solution;

(3-c) detecting the acidic potassium permanganate solutions in which the mercury vapor is enriched in step (3-b) to determine the total mercury content and the composition/content of stable mercury isotopes therein.

In accordance with some specific embodiments, in the method, the petroleum sample/hydrocarbon source rock sample is heated in a specially made quartz sample boat (123) for pyrolysis and cracking.

In accordance with some specific embodiments, in the method, the step (1-a) comprises heating the crude oil sample to the boiling point of the light hydrocarbon and holding the temperature until the light hydrocarbon volatilizes completely, and then gradually increasing the temperature at an interval of 80 to 120° C., with each temperature gradient maintained for 20 to 40 minutes until the crude oil sample becomes a solid residue, after that subjecting the solid residue to further cracking by increasing the temperature until the cracking is complete.

In accordance with some specific embodiments, in the method, step (1-a) further comprises sequentially absorbing the gas product released by heating the crude oil sample with a stannous chloride solution and with an acidic potassium permanganate solution, and passing the residual gas product after the absorption into a container containing a silica gel, and the stannous chloride solution in step (1-a) has a concentration of 15 to 25 w/v %.

In accordance with some specific embodiments, in the method, each of the stannous chloride solutions in step (1-b), step (2-b) and step (3-b) independently has a concentration of 15 to 25 w/v %.

In accordance with some specific embodiments, in the method, each of the acidic aqueous potassium permanganate solutions in step (1-a), step (2-a) and step (3-a) has an acid concentration of 10% and a potassium permanganate concentration of 4%, independently; each of the acidic aqueous potassium permanganate solutions in step (1-b), step (2-b) and step (3-b) has an acid concentration of an acid of 10% and a potassium permanganate concentration of 1%, independently, the acid is sulfuric acid.

In accordance with some specific embodiments, in the method, each of step (1-b), step (2-b) and step (3-b) comprises, independently, pumping a stannous chloride solution into the acidic potassium permanganate solution in which a crude oil is absorbed as collected in step (1-a), the acidic potassium permanganate solution in which a hydrocarbon source rock is absorbed as collected in step (2-a) and the acidic potassium permanganate solution in which a natural gas is absorbed as collected in step (3-a), using nitrogen gas as a carry gas, so as to reduce mercury to mercury vapor, and feeding the mercury vapor into the acidic aqueous potassium permanganate solution with nitrogen gas to purify and enrich the mercury vapor.

In accordance with some specific embodiments, in the method, the nitrogen gas used as a carry gas in each of step (1-b), step (2-b) and step (3-b) is subjected to mercury trapping treatment respectively, prior to contacting the acidic potassium permanganate solution collected in step (1-a), step (2-a) and step (3-a).

In accordance with some specific embodiments, in the method, each of step (1-c), step (2-d) and step (3-c) comprises detecting the acidic potassium permanganate solution in which the mercury vapor is enriched in each of step (1-b), step (2-b) and step (3-b) with a cold atomic fluorescence mercury detector and with a multi-collector inductively coupled plasma mass spectrometer, respectively.

In accordance with some specific embodiments, in the method, the natural gas in step (3-a) has a flow rate of 0.5 to 0.7 L/h.

In accordance with some specific embodiments, in the method, step (3-a) further comprises passing the natural gas firstly into the empty impact sampler and then passing the natural gas out from the empty impact sampler into three cascading acidic-potassium-permanganate absorption bottles to perform the three-stage cascading absorption, and passing the residual natural gas after absorption into a silica-gel impact sampler.

In accordance with some specific embodiments, in the method, step (3-a) further comprises controlling the time for three-stage cascading absorption for natural gas in step (3-a), so that the collected acidic potassium permanganate solution has a mercury content of equal to or greater than 1.0 ng/ml.

In accordance with some specific embodiments, in the method, step (2-c) comprises dry-pulverizing a hydrocarbon source rock sample and then adding the sample into aqua regia, heating for 2 hours at 95° C. for digestion, thereafter adding BrCl thereto, continuing to digest at 95° C. for 30 minutes, then standing for at least 24 hours and adding $NH_2OH \cdot HCl$ thereto to reduce excessive BrCl, left standing and taking a supernatant for detection.

In accordance with some specific embodiments, in the method, the detection is performed on the supernatant using a cold atomic fluorescence mercury detector and a multiple receive inductively couple plasma mass spectrometer.

In accordance with some specific embodiments, the method further comprises step (4) of: based on the detection results in step (1-c), step (2-d) and step (3-c), establishing the value range and the crucial parameters regarding the mercury isotope ratio in different genetic types of oil-gas, summarizing the mercury information characteristics in mass fractionation and mass-independent fractionation in different genetic types of oil-gas, and establishing an indicator chart for identification, so as to determine the oil-gas source, genesis and guide the exploration deployment.

In accordance with some specific embodiments, the method performs the detection by using the device for detecting mercury isotopes in crude oil according to any one of the present embodiments for detection.

In summary, the disclosure provides a method and a device for detecting mercury isotopes in oil-gas source. The method according to the present disclosure has the following advantages: it eliminates drawbacks in traditional methods for the determination of oil-gas source based on biomarker compounds or carbons, especially drawbacks in the loss of biomarker compounds in a process for, such as, thick oil and condensate oil. For oil-gas sources of high-over mature, the use of mercury isotope is the most effective to overcome difficulties in performing oil-gas source correlation due to the high-evolution biomarker evolutionary equilibrium. In addition, the three types of sources of crude oil, natural gas and hydrocarbon source rock can be collectively correlated.

DETAILED DESCRIPTION

In the following, a detailed description is provided for the implementation and beneficial effects of the present disclosure by the way of specific examples, which are intended to help a better understanding for the essence and features of the present invention and are not intended to limit the implementable scope of the present invention.

Example 1

Figure 1:
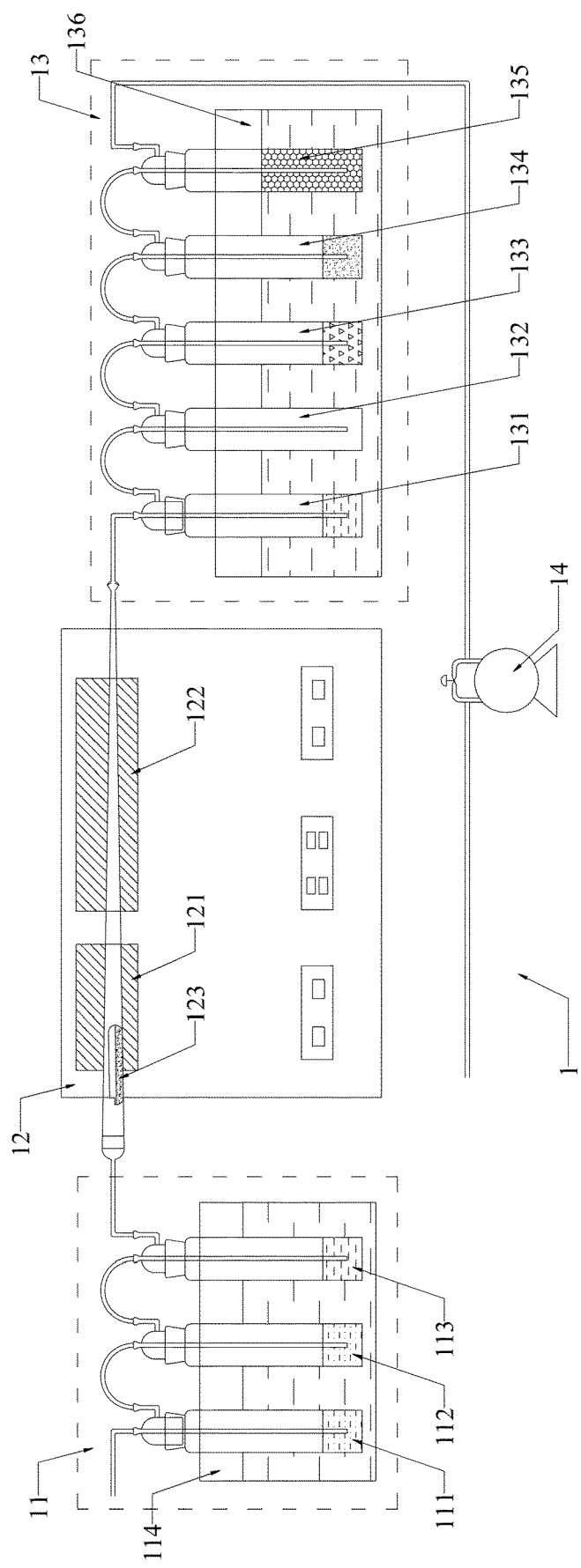
FIG. 1 is a schematic diagram of the enrichment-absorption system for mercury in crude oil/hydrocarbon source rock according to the present disclosure.
Figure 2:
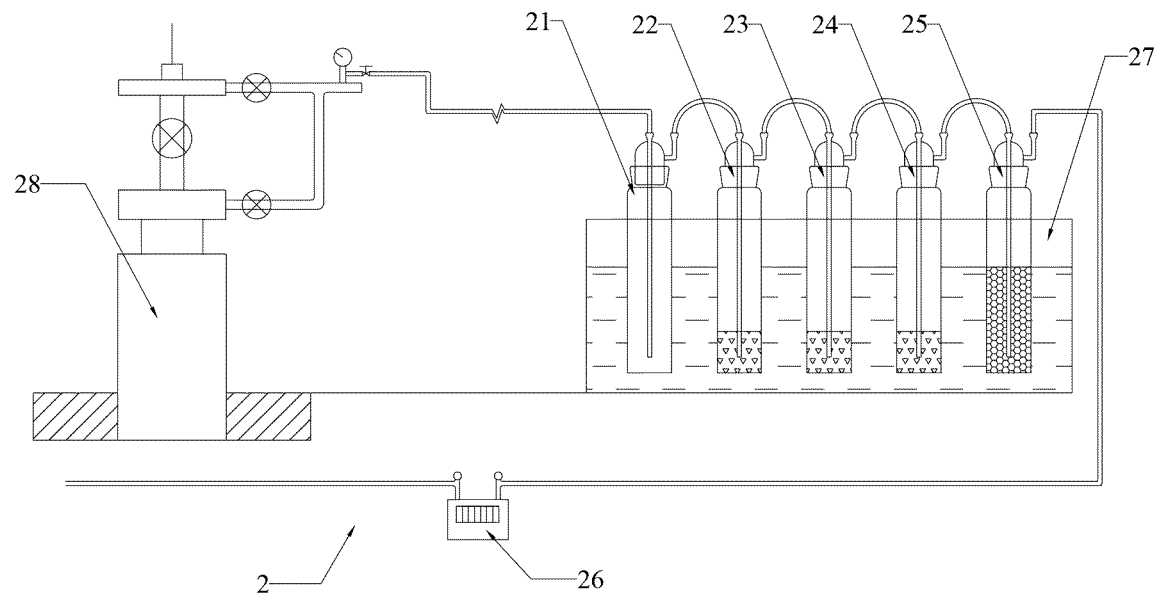
FIG. 2 is a schematic diagram of the enrichment-absorption system for mercury in natural gas according to the present disclosure.
Figure 3:
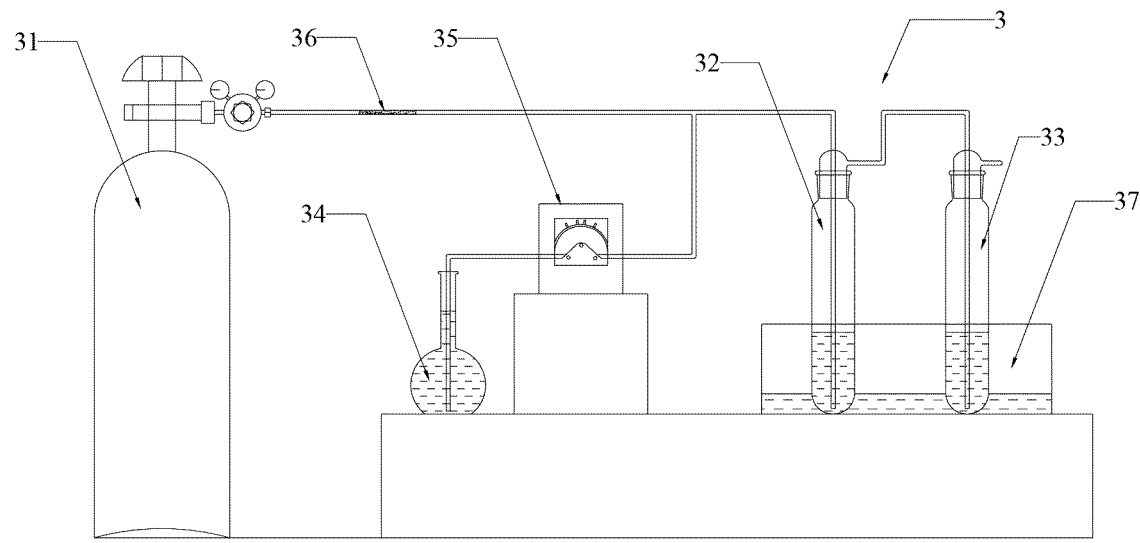
FIG. 3 is a schematic diagram of the secondary purification-enrichment system for mercury according to the present disclosure.

A device for detecting mercury isotopes in oil-gas sources, comprising two enrichment-absorption systems 1 for mercury in crude oil/hydrocarbon source rock (as shown in FIG. 1), an enrichment-absorption system 2 for mercury in natural gas (as shown in FIG. 2) and three secondary purification-enrichment system 3 for mercury (as shown in FIG. 3), wherein the two enrichment-absorption systems 1 for mercury in crude oil/hydrocarbon source rock are respectively the enrichment-absorption system for mercury in crude oil used for the enrichment and absorption for mercury in the crude oil and the enrichment-absorption system for mercury in hydrocarbon source rock used for the enrichment and absorption for mercury in the hydrocarbon source rock. The three secondary purification-enrichment systems 3 for mercury are respectively the secondary purification-enrichment system for mercury in crude oil used for the secondary purification and enrichment for mercury in crude oil, the secondary purification-enrichment system for mercury in hydrocarbon source rock used for the secondary purification and enrichment for mercury in hydrocarbon source rock, and the secondary purification-enrichment system for mercury in natural gas used for the secondary purification and enrichment for mercury in natural gas.

The enrichment-absorption system 1 for mercury in crude oil/hydrocarbon source rock comprises, connected in series by pipe lines, a first air-absorption bottle 111 containing aqua regia, a second air-absorption bottle 112 containing aqua regia and a third air-absorption bottle 113 containing an aqueous sodium hydroxide solution, a pyrolysis/cracking system 12, a first impact sampler 131 containing a stannous chloride solution, an empty impact sampler 132, a third impact sampler 133 containing an acidic potassium permanganate solution, a fourth impact sampler 134 containing an aqueous sodium hydroxide solution and an fifth impact sampler 135 containing a silica gel, and a vacuum pump 14; the pyrolysis/cracking system 12 includes a pyrolysis chamber 121 and a cracking chamber 122 connected in series with pipe lines; the pyrolysis chamber 121 is connected via a pipe line to the last air-absorption bottle in the connection order in the enrichment-absorption system 1 for mercury in crude oil/hydrocarbon source rock, and the cracking chamber 122 is connected via a pipe line to the first impact sampler in the connection order in the enrichment-absorption system 1 for mercury in crude oil/hydrocarbon source rock. The air-absorption bottles and the impact samplers are all made of borosilicate glass and are provided with a gas inlet and a gas outlet at the respective top thereof, wherein the gas inlet communicates with the inner space of the bottle through a glass tube which is provided inside the bottle and extends to the lower part of the bottle. The three air-absorption bottles are connected in series, with the gas outlet of the former air-absorption bottle connected to the gas inlet of the latter air-absorption bottle via a pipe line, the gas inlet of the first air-absorption bottle communicating with air, and the gas outlet of the last air-absorption bottle connected to the pyrolysis/cracking system 12 by a pipe line. The five impact samplers are connected in series, with the gas outlet of the former impact sampler connected to the gas inlet of the latter impact sampler by a pipe line, the gas inlet of the first impact sampler connected via a pipe line to the pyrolysis/cracking system 12, and the gas outlet of the last impact sampler connected to the vacuum pump 14 by a pipe line; The enrichment-absorption system 1 for mercury in crude oil/hydrocarbon source rock further comprises a sink 114 for air-absorption bottles, in which the three air-absorption bottles in the enrichment-absorption system 1 for mercury in crude oil/hydrocarbon source rock are disposed, and a sink 115 for impact samplers, in which the five impact samplers are disposed.

The enrichment-absorption system 2 for mercury in natural gas comprises, connected in series by pipe lines, an empty sixth impact sampler 21 and a seventh impact sampler 22 containing an acidic aqueous potassium permanganate solution, an eighth impact sampler 23 containing an acidic aqueous potassium permanganate solution, a ninth impact sampler 24 containing an acidic aqueous potassium permanganate solution, and a tenth impact sampler 25 containing a silica gel, wherein the sixth impact sampler 21 is connected to the natural gas outlet in a natural gas well, and the tenth impact sampler 25 is connected to a cumulative gas flow meter 26. The impact samplers are all made of borosilicate glass and are provided with a gas inlet and a gas outlet at the respective top thereof, wherein the gas inlet communicates with the inner space of the bottle through a glass tube which is provided inside the bottle and extends to the lower part of the bottle. The five impact samplers are connected in series, with the gas outlet of the former impact sampler connected to the gas inlet of the latter impact sampler by a pipe line, the gas inlet of the first impact sampler connected to the natural gas outlet from the natural gas well by a pipe line, and the gas outlet of the last impact sampler connected to the cumulative gas flow meter 26 by a pipe line. The enrichment-absorption system 2 for mercury in natural gas further comprises a sink 27 for the enrichment-absorption system 2 for mercury in natural gas, in which the five impact samplers in the enrichment-absorption system 2 for mercury in natural gas are disposed.

The secondary purification and enrichment system 3 comprises, connected in series by pipe lines, a nitrogen-gas cylinder 31, a collection bottle 32 with potassium permanganate absorption liquid in which mercury isotope is absorbed, and a secondary enrichment-absorption bottle 33 containing an acidic aqueous potassium permanganate solution, wherein the secondary purification-enrichment system 3 further comprises a stannous-chloride storage bottle 34, which is connected to a pipe line between the nitrogen-gas cylinder and the collection bottle 32 with potassium-permanganate absorption liquid via a peristaltic pump 35 and through a pipe line. The secondary purification-enrichment system further comprises a mercury-trapping gold tube 36 which is disposed on a pipe line connecting the nitrogen-gas cylinder 31 and the collection bottle 32 of potassium permanganate absorption liquid, and approximates to the gas outlet of the nitrogen-gas cylinder 31. The secondary purification-enrichment system 3 for mercury further comprises a sink 37 for the secondary purification-enrichment system 3 for mercury, in which the collection bottle 32 with potassium permanganate absorption liquid and the secondary enrichment-absorption 33 in the secondary purification-enrichment system 3 for mercury are disposed.

The device further comprises a cold atomic fluorescence mercury detector for detecting the total mercury content of the mercury enriched in the secondary enrichment-absorption bottle 22 and a multi-collector inductively-coupled plasma mass spectrometer for detecting the composition of stable isotopes of the mercury enriched in the secondary enrichment-absorption bottle 22.

In this example, the acidic aqueous potassium permanganate solution in the enrichment-absorption system 1 for mercury in crude oil/hydrocarbon source rock and the enrichment-absorption system 2 for mercury in natural gas have a potassium permanganate concentration of 1 w/v %, and an acid concentration of 10 v/v %, the acid is sulfuric acid; and the acidic aqueous potassium permanganate solutions in the secondary purification-enrichment system 3 for mercury have a potassium permanganate concentration of 4 w/v %, and an acid concentration of 10 v/v %, the acid is sulfuric acid. Each of the stannous chloride solution in the enrichment-absorption system 1 for mercury in crude oil/hydrocarbon source rock and the secondary purification-enrichment system 3 independently has a concentration of 20 w/v %; and the aqueous sodium hydroxide solution in the fourth impact sampler 134 has a concentration of 30 w/v %. The aqueous sodium hydroxide solution in the third air-absorption bottle 113 has a concentration of 30 w/v %.

The mercury isotopes in an oil-gas source is detected by using the device as above, which comprises the following steps:

(1-a) primary enrichment for mercury isotopes in crude oil: heating the crude oil sample to the boiling point of the light hydrocarbon and holding the temperature until the light hydrocarbon volatilizes completely, and then gradually increasing the temperature at an interval of 100° C., with each temperature gradient maintained for 30 minutes until the crude oil sample becomes a solid residue, after that subjecting the solid residue to further cracking by increasing the temperature until the cracking is complete; sequentially absorbing the gas product released by heating the crude oil sample with a stannous chloride solution (20 w/v %) and with acidic potassium permanganate solutions to enrich the mercury elements in the crude oil sample, and collecting all of the acidic potassium permanganate solutions in which mercury elements are enriched in step (1-a); and passing the residual gas product after the absorption into a container containing a silica gel;

(1-b) purification and enrichment for mercury isotopes in crude oil: pumping a stannous chloride solution into the acidic potassium permanganate solution in which a crude oil is absorbed as collected in step (1-a), using nitrogen gas as a carry gas, so as to reduce mercury to mercury vapor, and feeding the mercury vapor into an acidic aqueous potassium permanganate solution with nitrogen gas to purify and enrich the mercury vapor;

(1-c) detection for mercury isotopes in crude oil: detecting the acidic potassium permanganate solution in which the mercury vapor is enriched in step (1-b) with a cold atomic fluorescence mercury detector and with a multi-collector inductively coupled plasma mass spectrometer to determine the total mercury content and the composition/content of stable mercury isotopes therein;

(2-a) primary enrichment for mercury isotopes in hydrocarbon source rock: pulverizing a hydrocarbon source rock sample to 200 mesh, heating to 600° C., subjecting to pyrolysis and cracking until the petroleum in the hydrocarbon source rock sample is completely cracked, absorbing the gas released by heating the petroleum with an acidic aqueous potassium permanganate solution to enrich the mercury element from petroleum in the hydrocarbon source rock, and collecting all of the acidic potassium permanganate solutions in which the mercury element is enriched in step (2-a);

(2-b) purification and enrichment for mercury isotopes in hydrocarbon source rock: pumping a stannous chloride solution into the acidic potassium permanganate solution in which a hydrocarbon source rock is absorbed as collected in step (2-a), using nitrogen gas as a carry gas, so as to reduce mercury to mercury vapor, and feeding the mercury vapor into an acidic aqueous potassium permanganate solution with nitrogen gas to purify and enrich the mercury vapor;

(2-c) dry-pulverizing a hydrocarbon source rock sample and then adding the sample into aqua regia, heating for 2 hours at 95° C. for digestion, thereafter adding BrCl thereto, continuing to digest at 95° C. for 30 minutes, then standing for at least 24 hours and adding $NH_2OH \cdot HCl$ thereto to reduce excessive BrCl, left standing and taking a supernatant for detection;

(2-d) detection for mercury isotopes in crude oil: detecting the acidic potassium permanganate solutions in which the mercury vapor is enriched in steps (2-b) and (2-c) with a cold atomic fluorescence mercury detector and with a multi-collector inductively coupled plasma mass spectrometer to determine the total mercury content and the composition/content of stable mercury isotopes therein;

(3-a) primary enrichment for mercury isotopes in natural gas: subjecting natural gas to a three-stage cascading absorption with acidic aqueous potassium permanganate solutions at a flow rate for natural gas of 0.5 to 0.7 L/h, and collecting all of the acidic aqueous potassium permanganate solutions in which natural gas is absorbed in step (3-a); and controlling the time for three-stage cascading absorption for natural gas in step (3-a), so that the collected acidic potassium permanganate solution has a mercury content of equal to or greater than 1.0 ng/ml;

(3-b) mercury purification and enrichment: pumping a stannous chloride solution into the acidic potassium permanganate solution in which natural gas is absorbed as collected in step (3-a), using nitrogen gas as a carry gas, so as to reduce mercury to mercury vapor; and feeding the mercury vapor into an acidic aqueous potassium permanganate solution with nitrogen gas to purify and enrich the mercury vapor;

(3-c) detecting the acidic potassium permanganate solutions in which the mercury vapor is enriched in step (3-b) with a cold atomic fluorescence mercury detector and with a multi-collector inductively coupled plasma mass spectrometer to determine the total mercury content and the composition/content of stable mercury isotopes therein; and (4) based on the detection results in step (1-c), step (2-d) and step (3-c), establishing the value range and the critical parameters regarding the mercury isotope ratio in different genetic types of oil-gas, summarizing the mercury information characteristics in mass fractionation and mass-independent fractionation in different genetic types of oil-gas, and establishing an indicator chart for identification, to determine the oil-gas source and genesis and guide the exploration deployment.

The results are as follows:

The lower tertiary lacustrine hydrocarbon source rock, lacustrine crude oil and lacustrine natural gas (continental rock, oil and gas) in the typical Bohai Bay Basin, and the marine hydrocarbon source rock, marine crude oil and marine natural gas in the Tarim Basin are collected and subjected to mercury isotope analysis, respectively. The results are as follows.

Continental crude oil in Bohai Bay Basin:
Well No. NP101: $\delta^{202}Hg$ value: $-1.85‰\pm0.16‰$, $\Delta^{199}Hg$ value: $0.09‰\pm0.06‰$;
Well No. LPN1: $\delta^{202}Hg$ value: $-2.01‰\pm0.06‰$, $\Delta^{199}Hg$ value: $0.14‰\pm0.07‰$;
Well No. N11-2: $\delta^{202}Hg$ value: $-1.96‰\pm0.23‰$, $\Delta^{199}Hg$ value: $0.11‰\pm0.04‰$;

Associated gas in Bohai Bay Basin:
Well No. B101: $\delta^{202}Hg$ value: $-1.23‰\pm0.22‰$, $\Delta^{199}Hg$ value: $0.22‰\pm0.08‰$;
Well No. H2: $\delta^{202}Hg$ value: $-0.32‰\pm0.16‰$, $\Delta^{199}Hg$ value: $0.22‰\pm0.05‰$;
Well No. F9: $\delta^{202}Hg$ value: $-2.64‰\pm0.13‰$, $\Delta^{199}Hg$ value: $0.24‰\pm0.02‰$;

Hydrocarbon source rocks from sha-3 member in Bohai Bay Basin:
Well No. G11: $\delta^{202}Hg$ value: $-0.23‰\pm0.12‰$, $\Delta^{199}Hg$ value: $0.26‰\pm0.10‰$;
Well No. N38: $\delta^{202}Hg$ value: $-0.32‰\pm0.14‰$, $\Delta^{199}Hg$ value: $0.21‰\pm0.06‰$;

Marine crude oil in Tarim Basin:
Well No. FY101: $\delta^{202}Hg$ value: $-0.17‰\pm0.12‰$, $\Delta^{199}Hg$ value: $0.31‰\pm0.08‰$;
Well No. ZG83: $\delta^{202}Hg$ value: $0.09‰\pm0.32‰$, $\Delta^{199}Hg$ value: $0.39‰\pm0.05‰$;
Well No. H701: $\delta^{202}Hg$ value: $0.21‰\pm0.09‰$, $\Delta^{199}Hg$ value: $0.36‰\pm0.09‰$;

Marine natural gas in Tarim Basin:
Well No. TZ62: $\delta^{202}Hg$ value: $-0.12‰\pm0.11‰$, $\Delta^{199}Hg$ value: $0.31‰\pm0.07‰$;
Well No. ZG171: $\delta^{202}Hg$ value: $0.06‰\pm0.22‰$, $\Delta^{199}Hg$ value: $0.36‰\pm0.04‰$;
Well No. H15: $\delta^{202}Hg$ value: $0.18‰\pm0.04‰$, $\Delta^{199}Hg$ value: $0.32‰\pm0.06‰$;

Marine hydrocarbon source rocks in Tarim Basin:
Well No. KL1: $\delta^{202}Hg$ value: $0.19‰\pm0.11‰$, $\Delta^{199}Hg$ value: $0.31‰\pm0.06‰$;
Well No. SARK: $\delta^{202}Hg$ value: $0.22‰\pm0.22‰$, $\Delta^{199}Hg$ value: $0.32‰\pm0.04‰$;
Well No. H701: $\delta^{202}Hg$ value: $0.21‰\pm0.09‰$, $\Delta^{199}Hg$ value: $0.36‰\pm0.09‰$;

The analysis results are in good agreement with the crude oil types. Therefore, the $\delta^{202}Hg$ value of $-0.2‰$ and $\Delta^{199}Hg$ value of $3‰$ for crude oils may be used as indices to distinguish continental oil-gas and marine oil-gas. If the value is respectively larger than the index, it is a marine oil, conversely, it is a continental oil.

What is claimed is:

1. A device for detecting mercury isotopes in an oil-gas source, comprising:
at least one enrichment-absorption system for mercury in crude oil/hydrocarbon source rock, an enrichment-absorption system for mercury in natural gas and at least one secondary purification-enrichment system for mercury;
the at least one enrichment-absorption system for mercury in crude oil/hydrocarbon source rock comprises three air-absorption bottles, a pyrolysis/cracking system, five impact samplers, and a vacuum pump, which are connected in series by pipe lines;
the enrichment-absorption system for mercury in natural gas comprises five impact samplers connected in series, wherein the first impact sampler is connected to a natural gas outlet from a natural gas well and the last impact sampler is connected to a cumulative gas flow meter;
the at least one secondary purification-enrichment system for mercury comprises a nitrogen-gas cylinder, a collection bottle with potassium permanganate absorption liquid in which mercury isotope is absorbed, and a secondary enrichment-absorption bottle containing an acidic aqueous potassium permanganate solution, which are connected in series by pipe lines, wherein the at least one secondary purification-enrichment system further comprises a stannous-chloride storage bottle, which is connected to a pipe line between the nitrogen-gas cylinder and the collection bottle with potassium-permanganate absorption liquid via a peristaltic pump and through a pipe line.

2. The device according to claim 1, wherein the five impact samplers in the at least one enrichment-absorption system for mercury in crude oil/hydrocarbon source rock are, in a connection order, respectively a first impact sampler containing a stannous chloride solution, an empty impact sampler, a third impact sampler containing an acidic potassium permanganate solution, a fourth impact sampler containing an aqueous sodium hydroxide solution and an fifth impact sampler containing a silica gel, wherein the first impact sampler is connected via a pipe line to the pyrolysis/cracking system; and the five impact samplers in the enrichment-absorption system for mercury in natural gas are, in a connection order, respectively an empty sixth impact sampler and a seventh impact sampler containing an acidic aqueous potassium permanganate solution, an eighth impact sampler containing an acidic aqueous potassium permanganate solution, a ninth impact sampler containing an acidic aqueous potassium permanganate solution, and a tenth impact sampler containing a silica gel;

wherein the three air-absorption bottles in the at least one enrichment-absorption system for mercury in crude oil/hydrocarbon source rock are, in a connection order, respectively a first air-absorption bottle containing aqua regia, a second air-absorption bottle containing aqua regia and a third air-absorption bottle containing an aqueous sodium hydroxide solution, and the pyrolysis/cracking system is connected to the third air-absorption bottle through a pipe line.

3. The device according to claim 2, wherein the acidic aqueous potassium permanganate solutions in the at least one enrichment-absorption system for mercury in crude oil/hydrocarbon source rock and the enrichment-absorption system for mercury in natural gas have a potassium permanganate concentration of 1 w/v %, and an acid concentration of 10 v/v %, the acid is sulfuric acid; and the acidic aqueous potassium permanganate solutions in the at least one secondary purification-enrichment system for mercury have a potassium permanganate concentration of 4 w/v %, and an acid concentration of 10 v/v %, the acid is sulfuric acid;

wherein each of the stannous chloride solution in the at least one enrichment-absorption system for mercury in crude oil/hydrocarbon source rock and the at least one secondary purification-enrichment system independently has a concentration of 15 to 25 w/v %;

and the aqueous sodium hydroxide solution in the fourth impact sampler has a concentration of 30 w/v %;

wherein the aqueous sodium hydroxide solution in the third air-absorption bottle has a concentration of 30 w/v %.

4. The device according to claim 1, wherein the pyrolysis/cracking system comprises a pyrolysis chamber and a cracking chamber connected in series with pipe lines; said pyrolysis chamber is connected via a pipe line to a last air-absorption bottle in a connection order in the at least one enrichment-absorption system for mercury in crude oil/hydrocarbon source rock, and the cracking chamber is connected via a pipe line to a first impact sampler in a connection order in the at least one enrichment-absorption system for mercury in crude oil/hydrocarbon source rock.

5. The device according to claim 1, wherein each of the three air-absorption bottles and five impact samplers in the at least one enrichment-absorption system for mercury in crude oil/hydrocarbon source rock, and the five impact samplers in the enrichment-absorption system for mercury in natural gas is a borosilicate glass bottle and is provided with a gas inlet and a gas outlet at a respective top thereof, wherein the gas inlet communicates with an inner space of the bottle through a glass tube which is provided inside the bottle and extends to a lower part of the bottle.

6. The device according to claim 4, wherein, in the at least one enrichment-absorption system for mercury in crude oil/hydrocarbon source rock, three air-absorption bottles are connected in series, with the gas outlet of a former air-absorption bottle connected to the gas inlet of a latter air-absorption bottle via a pipe line, the gas inlet of the first air-absorption bottle communicating with air, and the gas outlet of the last air-absorption bottle connected to the pyrolysis/cracking system by a pipe line; the five impact samplers are connected in series, with the gas outlet of a former impact sampler connected to the gas inlet of a latter impact sampler by a pipe line, the gas inlet of the first impact sampler connected via a pipe line to the pyrolysis/cracking system, and the gas outlet of the last impact sampler connected to the vacuum pump by a pipe line;

in the enrichment-absorption system for mercury in natural gas, the five impact samplers are connected in series, with the gas outlet of a former impact sampler connected to the gas inlet of a latter impact sampler by a pipe line, the gas inlet of the first impact sampler connected to the natural gas outlet of the natural gas well by a pipe line, and the gas outlet of the last impact sampler connected to the cumulative gas flow meter by a pipe line.

7. The device according to claim 1, wherein the at least one secondary purification-enrichment system further comprises a mercury-trapping gold tube which is disposed on a pipe line connecting the nitrogen-gas cylinder and the collection bottle with potassium permanganate absorption liquid, and approximates to a gas outlet of the nitrogen-gas cylinder.

8. The device according to claim 1, further comprising a detector for detecting total mercury content of mercury enriched in the secondary enrichment-absorption bottle and a detector for detecting composition of stable isotopes of the mercury enriched in the secondary enrichment-absorption bottle.

9. The device according to claim 8, wherein the detector for detecting the total mercury content of the mercury enriched in the secondary enrichment-absorption bottle is a cold atomic fluorescence mercury detector, and the detector for detecting the composition of stable isotopes of the mercury enriched in the secondary enrichment-absorption bottle is a multi-collector inductively-coupled plasma mass spectrometer.

10. The device according to claim 1, comprising two enrichment-absorption systems for mercury in crude oil/hydrocarbon source rock, and three secondary purification-enrichment systems for mercury, wherein the two enrichment-absorption systems for mercury in crude oil/hydrocarbon source rock are respectively used for the enrichment and absorption for mercury in the crude oil and the enrichment and absorption for mercury in the hydrocarbon source rock, and the three secondary purification-enrichment systems for mercury are respectively used for the secondary purification and enrichment for mercury in crude oil, the secondary purification and enrichment for mercury in hydrocarbon source rock, and the secondary purification and enrichment for mercury in natural gas.

11. A method for detecting mercury isotopes in an oil-gas source, comprising the steps of:
(1-a) primary enrichment for mercury isotopes in crude oil: heating a crude oil sample to perform pyrolysis and cracking until the crude oil sample is completely cracked, absorbing gas released by heating the crude oil sample with acidic aqueous potassium permanganate solutions to enrich the mercury element in the crude oil sample, and collecting all of the acidic potassium permanganate solutions in which the mercury element is enriched in step (1-a);

(1-b) purification and enrichment for mercury isotopes in crude oil: reducing the mercury absorbed by the acidic potassium permanganate solutions in the step (1-a) to mercury vapor with a stannous chloride solution, and then purifying and enriching the mercury vapor by using an acidic aqueous potassium permanganate solution;

(1-c) detection for mercury isotopes in crude oil: detecting the acidic potassium permanganate solution in which the mercury vapor is enriched in step (1-b) to determine total mercury content and composition/content of stable mercury isotopes therein;

(2-a) primary enrichment for mercury isotopes in hydrocarbon source rock: pulverizing a hydrocarbon source rock sample to 200 mesh, heating to 600° C., subjecting to pyrolysis and cracking until petroleum in the hydrocarbon source rock sample is completely cracked, absorbing gas released by heating the petroleum with acidic aqueous potassium permanganate solutions to enrich mercury element from petroleum in the hydrocarbon source rock sample, and collecting all of the acidic potassium permanganate solutions in which the mercury element is enriched in step (2-a);

(2-b) purification and enrichment for mercury isotopes in hydrocarbon source rock: reducing the mercury absorbed by the acidic potassium permanganate solutions in the step (2-a) to mercury vapor with a stannous chloride solution, and then purifying and enriching the mercury vapor by using an acidic aqueous potassium permanganate solution;

(2-c) detection of mercury isotopes in hydrocarbon source rock: detecting the acidic potassium permanganate solution in which the mercury vapor is enriched in step (2-b) to determine total mercury content and composition/content of stable mercury isotopes therein;

(3-a) primary enrichment for mercury isotopes in natural gas: subjecting natural gas to a three-stage cascading absorption with acidic aqueous potassium permanganate solutions, and collecting all of the acidic aqueous potassium permanganate solutions in which natural gas is absorbed in step (3-a);

(3-b) mercury purification and enrichment: reducing the mercury absorbed by the acidic aqueous potassium permanganate solutions in the step (3-a) to mercury vapor with a stannous chloride solution, and then purifying and enriching the mercury vapor by using an acidic potassium permanganate aqueous solution;

(3-c) detecting the acidic potassium permanganate solution in which the mercury vapor is enriched in step (3-b) to determine total mercury content and composition/content of stable mercury isotopes therein.

12. The method according to claim 11, wherein the step (1-a) comprises heating the crude oil sample to boiling point of light hydrocarbon and holding temperature until the light hydrocarbon volatilizes completely, and then gradually increasing the temperature at an interval of 80 to 120° C., with each temperature gradient maintained for 20 to 40 minutes until the crude oil sample becomes a solid residue, after that subjecting the solid residue to further cracking by increasing the temperature until the cracking is complete.

13. The method according to claim 11, wherein step (1-a) further comprises sequentially absorbing gas product released by heating the crude oil sample with a stannous chloride solution and with an acidic potassium permanganate solution, and passing residual gas product after the absorption into a container containing a silica gel, and the stannous chloride solution in step (1-a) has a concentration of 15 to 25 w/v %.

14. The method according to claim 11, wherein each of the stannous chloride solutions in step (1-b), step (2-b) and step (3-b) independently has a concentration of 15 to 25 w/v %;

wherein each of the acidic aqueous potassium permanganate solutions in step (1-a), step (2-a) and step (3-a) has an acid concentration of 10% and a potassium permanganate concentration of 4%, independently; each of the acidic aqueous potassium permanganate solutions in step (1-b), step (2-b) and step (3-b) has an acid concentration of 10% and a potassium permanganate concentration of 1%, independently, wherein the acid is sulfuric acid.

15. The method according to claim 11, wherein each of step (1-b), step (2-b) and step (3-b) comprises, independently, pumping a stannous chloride solution into the acidic potassium permanganate solutions in which a crude oil is absorbed as collected in step (1-a), the acidic potassium permanganate solutions in which a hydrocarbon source rock is absorbed as collected in step (2-a) and the acidic potassium permanganate solutions in which a natural gas is absorbed as collected in step (3-a), using nitrogen gas as a carry gas, so as to reduce mercury to mercury vapor, and feeding the mercury vapor into the acidic aqueous potassium permanganate solution with nitrogen gas to purify and enrich the mercury vapor;

wherein the nitrogen gas used as a carry gas in each of step (1-b), step (2-b) and step (3-b) is subjected to mercury trapping treatment respectively, prior to contacting the acidic potassium permanganate solutions collected in step (1-a), step (2-a) and step (3-a).

16. The method according to claim 11, wherein each of step (1-c), step (2-c) and step (3-c) comprises detecting the acidic potassium permanganate solution in which the mercury vapor is enriched in each of step (1-b), step (2-b) and step (3-b) with a cold atomic fluorescence mercury detector and a multi-collector inductively coupled plasma mass spectrometer, respectively.

17. The method according to claim 11, wherein step (3-a) further comprises passing the natural gas firstly into an empty impact sampler and then passing the natural gas out from the empty impact sampler into three cascading acidic-potassium-permanganate absorption bottles to perform the three-stage cascading absorption, and passing residual natural gas after absorption into a silica-gel impact sampler;

wherein step (3-a) further comprises controlling time for three-stage cascading absorption for natural gas in step (3-a), so that the collected acidic potassium permanganate solutions have a mercury content of equal to or greater than 1.0 ng/ml, wherein the natural gas in step (3-a) has a flow rate of 0.5 to 0.7 L/h.

18. The method according to claim 11, further comprising step (4) of: based on detection results in step (1-c), step (2-c) and step (3-c), establishing a value range and critical parameters regarding a mercury isotope ratio in different genetic types of oil-gas, summarizing mercury information characteristics in mass fractionation and mass-independent fractionation in different genetic types of oil-gas, and establishing an indicator chart for identification, so as to determine oil-gas source and genesis and guide an exploration deployment.

19. The method according to claim 11, wherein the method performs the detection by using a device comprising:
- at least one enrichment-absorption system for mercury in crude oil/hydrocarbon source rock, an enrichment-absorption system for mercury in natural gas and at least one secondary purification-enrichment system for mercury;
- the at least one enrichment-absorption system for mercury in crude oil/hydrocarbon source rock comprises three air-absorption bottles, a pyrolysis/cracking system, five impact samplers, and a vacuum pump, which are connected in series by pipe lines;
- the enrichment-absorption system for mercury in natural gas comprises five impact samplers connected in series, wherein the first impact sampler is connected to a natural gas outlet from a natural gas well and the last impact sampler is connected to a cumulative gas flow meter;
- the at least one secondary purification-enrichment system for mercury comprises a nitrogen-gas cylinder, a collection bottle with potassium permanganate absorption liquid in which mercury isotope is absorbed, and a secondary enrichment-absorption bottle containing an acidic aqueous potassium permanganate solution, which are connected in series by pipe lines, wherein the at least one secondary purification-enrichment system further comprises a stannous-chloride storage bottle, which is connected to a pipe line between the nitrogen-gas cylinder and the collection bottle with potassium-permanganate absorption liquid via a peristaltic pump and through a pipe line.

* * * * *